United States Patent [19]

Sherman

[11] Patent Number: 5,311,883
[45] Date of Patent: May 17, 1994

[54] SANITARY SHIELD FOR DEDICATED MAMMOGRAPHY APPARATUS

[76] Inventor: Eleanor Sherman, 283 Murray Ave., Larchmont, N.Y. 10583

[21] Appl. No.: 972,639

[22] Filed: Nov. 6, 1992

[51] Int. Cl.⁵ .......................... A61F 5/37; A61B 19/00
[52] U.S. Cl. ..................................... 128/846; 128/849
[58] Field of Search ............................ 128/849–856, 128/653.1, 754; 378/37; 623/8

[56] References Cited

U.S. PATENT DOCUMENTS

| | | | |
|---|---|---|---|
| 3,971,950 | 7/1976 | Evans | 378/37 |
| 4,063,102 | 12/1977 | Ronci | 378/37 |
| 4,090,084 | 5/1978 | Epstein | 378/37 |
| 4,259,585 | 3/1981 | Novak | 378/37 |
| 4,599,738 | 7/1986 | Panetta | 378/37 |
| 4,962,515 | 10/1990 | Kopans | 378/37 |
| 4,979,196 | 12/1990 | Lieutaud | 378/37 |
| 5,081,657 | 1/1992 | Klawitter | 378/37 |
| 5,136,623 | 8/1992 | Hixson | 378/37 |

*Primary Examiner*—Michael A. Brown
*Attorney, Agent, or Firm*—Martin J. Spellman, Jr.

[57] ABSTRACT

A sanitary shield for a dedicated mammography x-ray machine compression paddle that includes a generally rectangular pan shaped, substantially transparent non x-ray attenuating thermoplastic plastic cover having a generally flat planar surface, and walls extending normally from the planar surface to a rim, an inwardly extending flange formed integrally in the walls and spaced slightly from the rim, the walls are dimensioned so as to extend around the sides of the compression paddle.

3 Claims, 4 Drawing Sheets

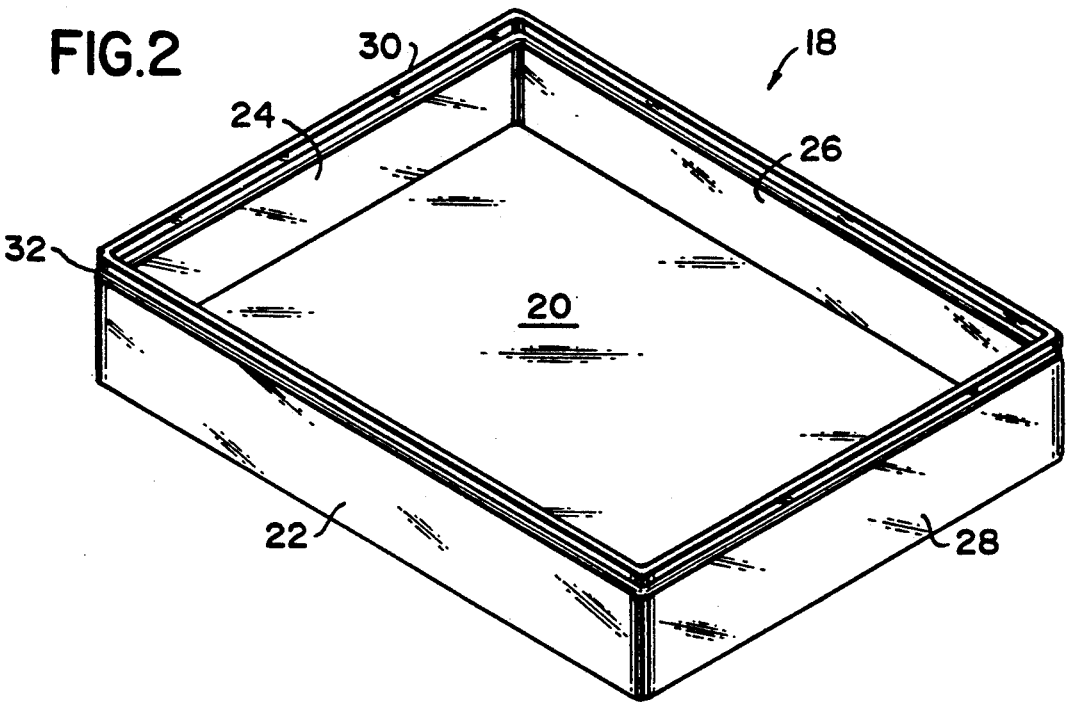
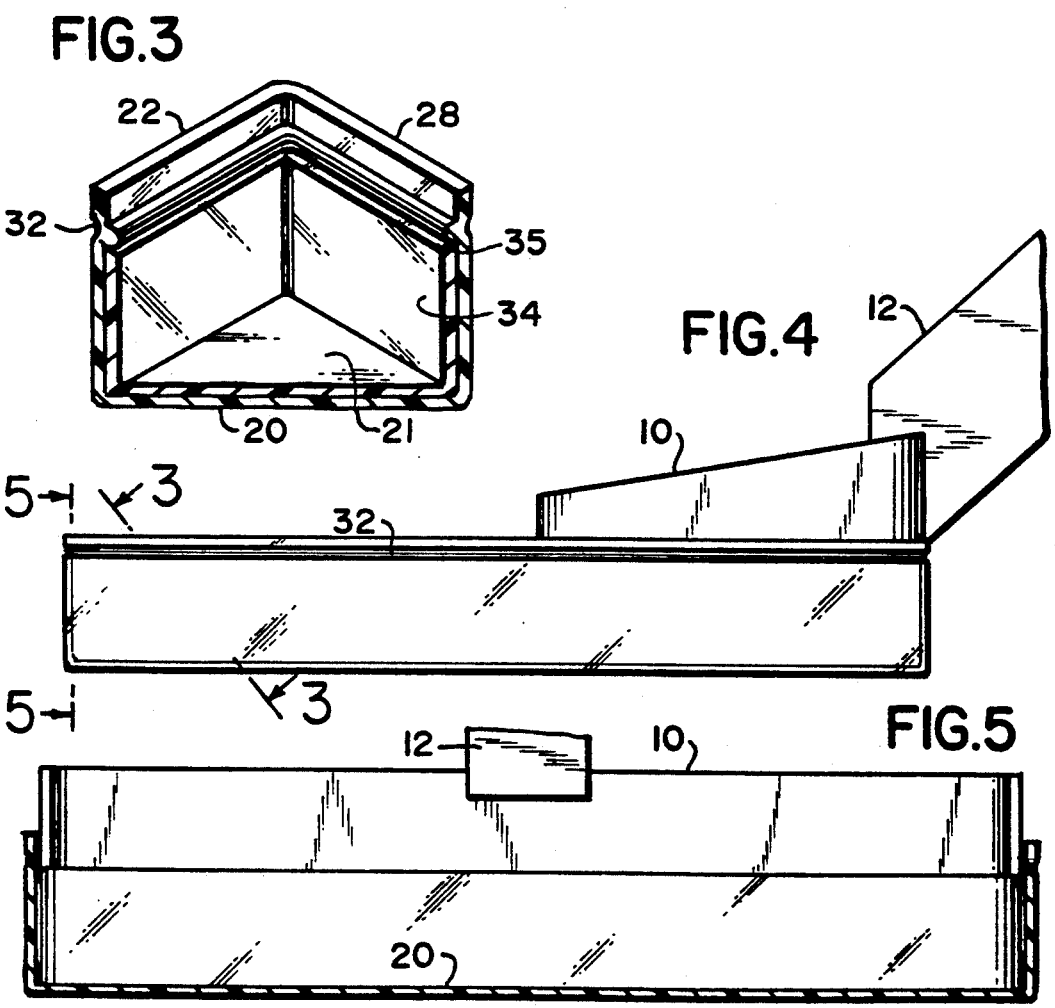

SANITARY SHIELD FOR DEDICATED MAMMOGRAPHY APPARATUS

BACKGROUND OF THE INVENTION

1. Field of the Invention

This invention is concerned with dedicated mammography x-ray apparatus and particular the mammography buckys and compression paddles of such apparatus. In the utilization of such apparatus, the flesh of the patient being tested comes in direct contact with the surfaces of the bucky and compression paddle and thus there is the risk that the body fluids from cuts, abrasions, nipple discharges or other sources will contaminate the compression paddle and/or bucky with blood born pathogens in these fluids. Thus the use of such apparatus without sanitary protection can allow HIV virus, hepatitis and other diseases to be transmitted from patient to patient or to operators and other workers.

2. Prior Art

Up to the present time, no effective shielding protection has been utilized. Any protection, of course, should not cause any deleterious attenuation of the x-ray beams. While some x-ray cassette covers of plastic film have been used, there are no shields available for the specific use on mammography x-ray apparatus. At present there is no effective way of disinfecting the apparatus because of potential damage to the machine materials and/or electrical components. Cleansing chemicals often tend to pit the plastic components.

SUMMARY OF THE INVENTION

The present invention provides sanitary shielding for dedicated mammography x-ray apparatus which is readily removed and changed following each patient use. The shielding is relatively inexpensive and may be disposed of after each use or may be sterilized by autoclaving and reused. The shielding of the present invention provides an inexpensive and effective means to protect the bucky and compression paddles of dedicated mammography x-ray apparatus from contamination by contact with patient body fluids without causing any deleterious attenuation of the x-ray beams.

The shielding cover of the present invention comprises generally rectangular pan shaped snap on plastic covers for the sides and lower horizontal surface of the compression paddle, and the front side and lateral sides, and top horizontal surface of the bucky. Suitable material is Lexan brand polycarbonate about 4 mil to 50 mil in thickness preferably about 10 mil–30 mil in thickness, and most preferred about 15 mil–25 mil. Thicker material can be used, but it becomes costly and flexibility diminishes too much. This material will not attenuate the x-ray beam. Other transparent non x-ray attenuating plastic sheet material such as polyethylene or glycol modified polyethylene terephthalate (PETG) and polypropylene may be used. All the surfaces apparatus which might be contacted by the patient's body during the x-ray procedure are covered.

The shielding covers are dimensioned to readily slide over the bucky and compression paddle from the top and bottom respectively. Each has its sides formed with an inwardly extending flange adjacent the rim of the sides and extending inwardly sufficiently to grasp the sides or remote planar surface of the bucky or compression paddle. The covers are made using known vacuum molding techniques.

BRIEF DESCRIPTION OF THE DRAWING

In the accompanying drawing which forms a part of this specification;

FIG. 2 is a perspective view of the shield cover for the compression paddle;

FIG. 3 is an enlarged sectional view of a corner and two sides of the compression paddle and shield cover along line 3—3 of FIG. 4 showing the inward flange securing the cover;

FIG. 4 is a side plan view of the compression paddle shield cover in place;

FIG. 5 is a front sectional view of the compression paddle shield cover in place on the paddle along line 5—5 of FIG. 4;

DESCRIPTION OF ILLUSTRATIVE SPECIFIC EMBODIMENT

Figure 1:
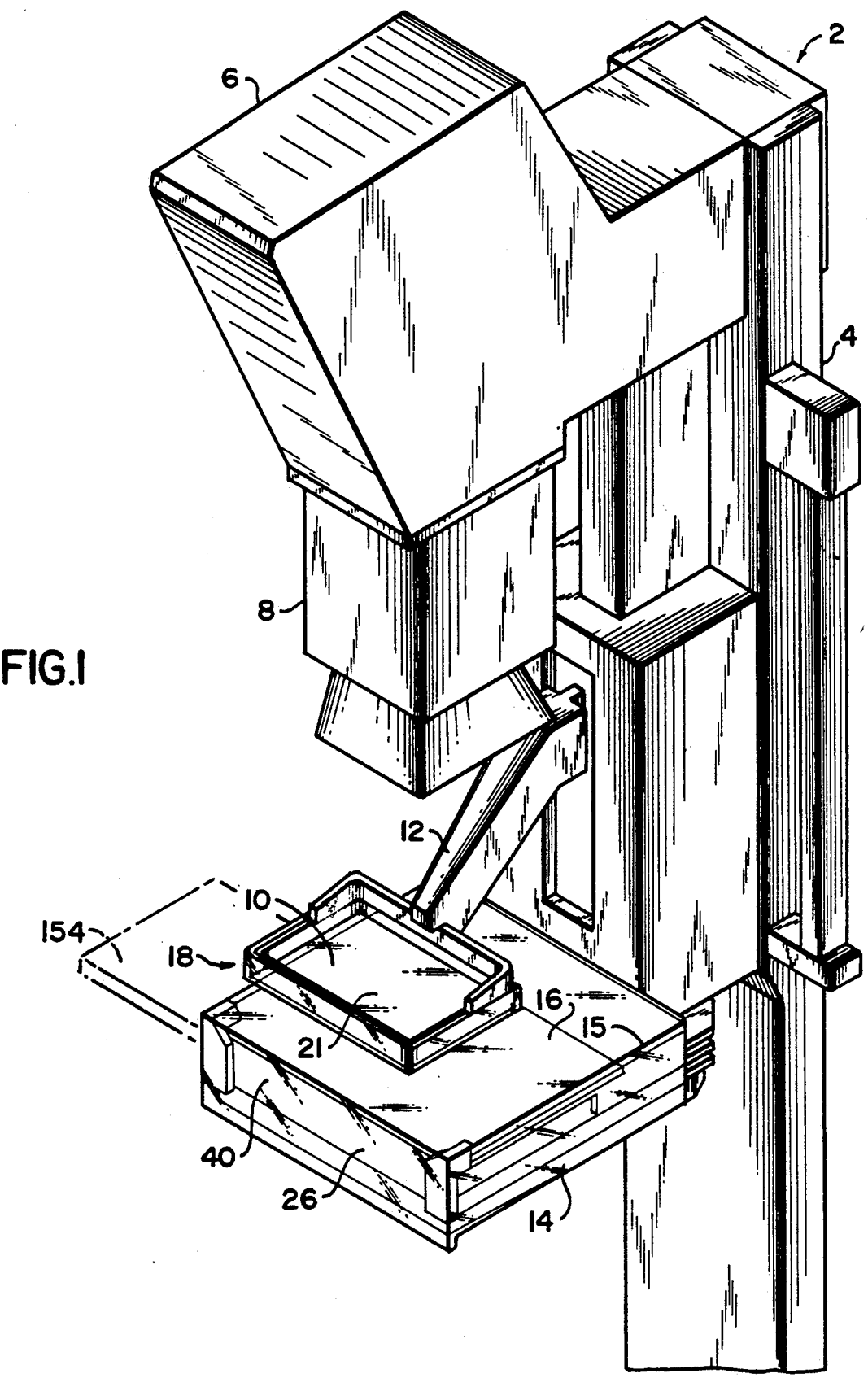
FIG. 1 is a perspective view of a mammography x-ray machine showing the shields of the present invention in place over the bucky and compression paddle.
Figure 6:
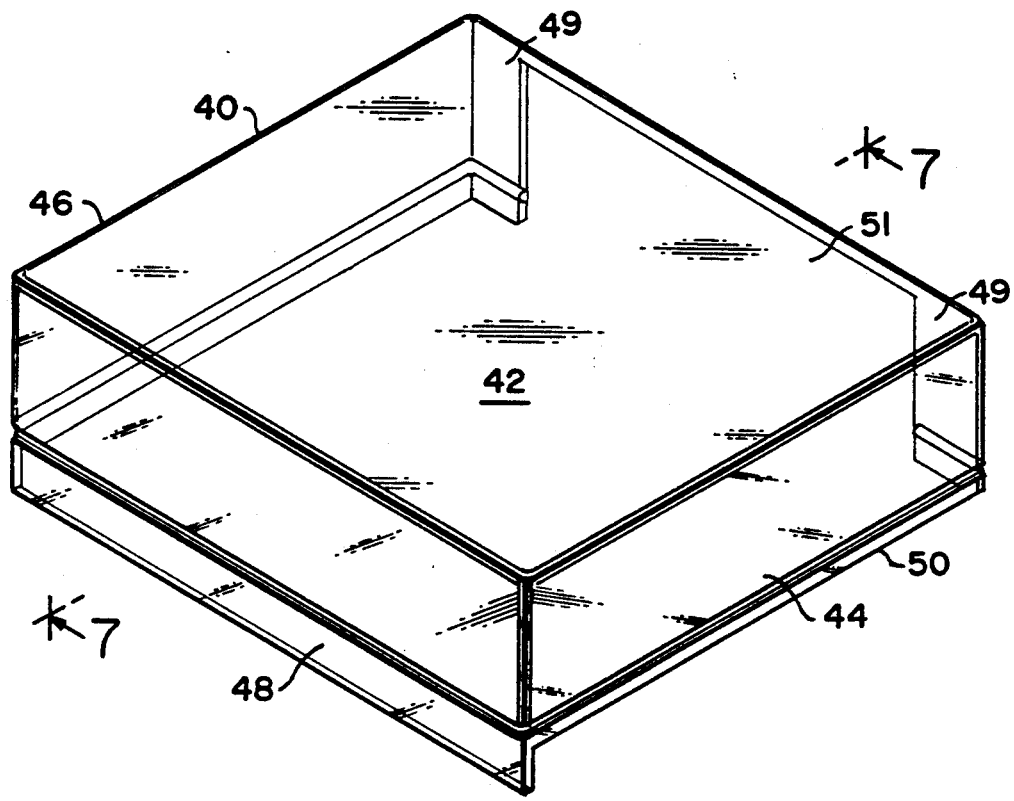
FIG. 6 is a perspective view of the bucky shield cover.
Figure 7:
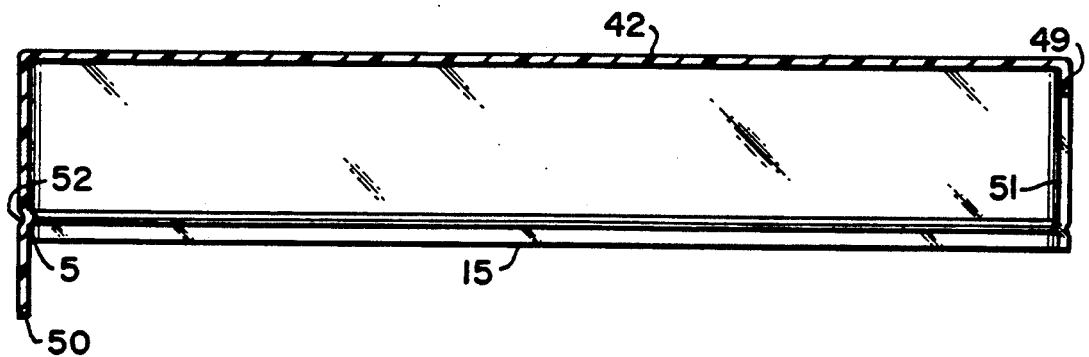
FIG. 7 is a side sectional view of the bucky shield cover along line 7—7 of FIG. 6.

In FIG. 1 of the accompanying drawing, a typical dedicated mammography x-ray apparatus 2 is shown and includes the adjustable frame section 4, tiltable head 6, x-ray source 8, compression paddle 10, compression paddle arm 12 and the x-ray plate bucky 14 on which the x-ray film plate 16 is secured. In use, the patient's breast are placed on the plate 16 carried on the bucky 14 and the compression paddle arm 12 lowered to move the paddle 10 down on top of the breasts.

The shield cover 18 on the compression paddle 10 includes the flat base section 20 joined to the sides 22, 24, 26, and 28 which extend upwardly to a rim 30. Slightly below the rim 30 an inwardly extending flange 32 is formed in the side walls 22, 24, 26, and 28 as shown best in FIG. 4. The cover 18 is vacuum formed from 20 mil polycarbonate sheet material.

The flange 32 is dimensioned so as to slidingly engage the sides 34 of the paddle 10 as it is placed over the paddle 10 as shown. The contact between the flange 32 and sides 34 of the paddle 10 is sufficient to hold the cover 18 in place on the paddle 10. It is preferred however that the cover 18 be pushed on so that the flat base section 20 is in contact with the horizontal base section 21 of the paddle 10 and that the flange 32 engage the top surface edge 35 of the paddle 10.

The shield cover 40 for the bucky 14 is formed in a similar manner. It has a flat pan base section 42 which covers the top 15 of the bucky 14 and downwardly extending walls 44 and 46, 48 and 49. The front wall 48 extends downwardly more than the others to give added protection in the most vulnerable area.

The sides 44, 46, 48 and 49 the bucky shield cover 40 extend downwardly to a rim 50. Slightly above the rim 50, an inwardly extending flange 52 is formed in the sides. The rear side 49 may be shorter and/or have an opening 51 to accommodate 2 the design of the machine.

The flange 52 is dimensioned to slidingly engage the sides 17, 19, and the front 21 side of the bucky 14. As the cover 40 is pushed onto the bucky 14, the flange 52 grasps the walls of the bucky so as to be slidingly held in place.

As the cover 40 is pushed fully down over the bucky 14, the flange 52 will engage the bottom surface edges of the bucky 14.

The shields 18 and 40 are placed over the compression paddle 10 and bucky 14 prior to each patient use and removed thereafter and new ones put in place for the next patient use.

Figure 8:
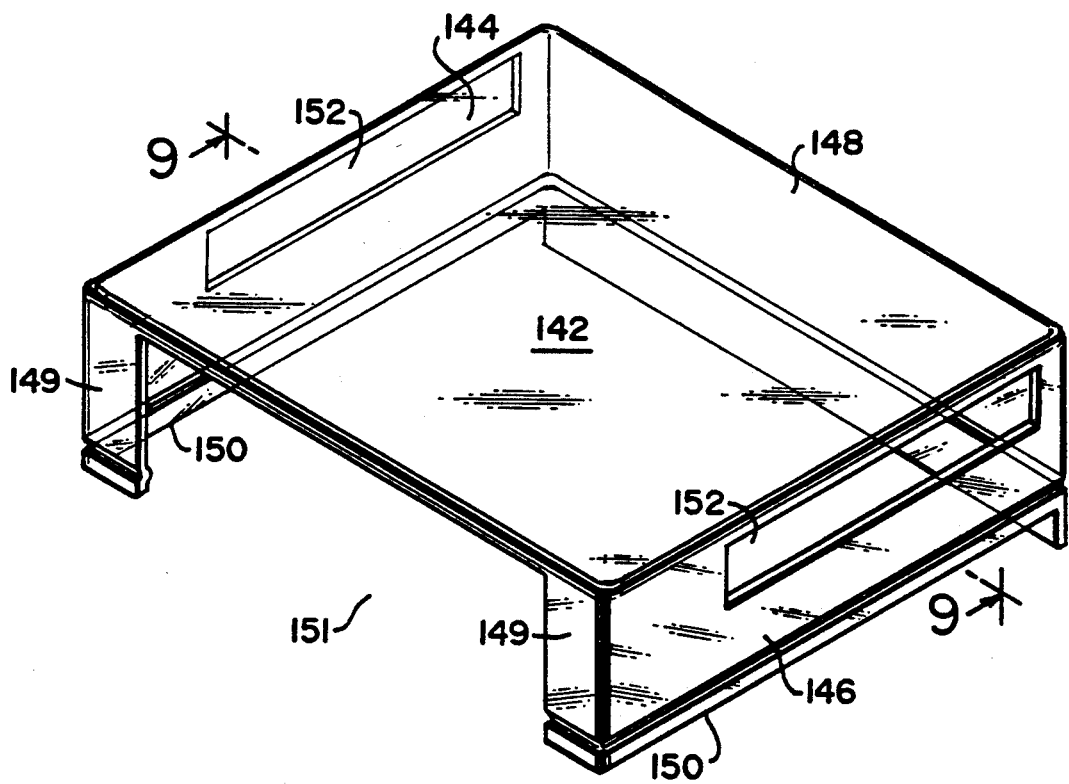
FIG. 8 is a perspective view of an alternative embodiment of the bucky shield cover with slots in the lateral sides for inserting and removing x-ray film plates.
Figure 9:
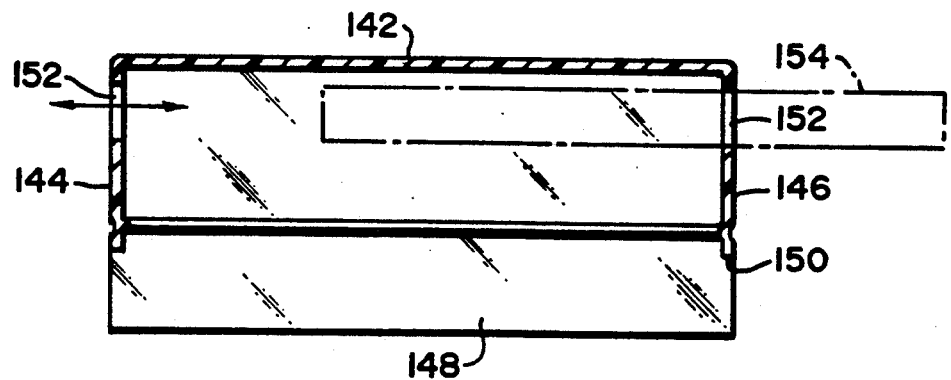
FIG. 9 is a sectional view along lines 9—9 of FIG. 8.

In FIGS. 8-9, an alternative embodiment of the bucky shield cover is shown. This embodiment provides slots in the lateral sides to allow access to change x-ray film plates carried in the bucky without having to remove the cover for access.

The cover has a flat pan base 142, side walls 144 and 146, front wall 148 and rear wall 149 with opening 151. The sides 144 and 146 are provided with horizontal slots 152 dimensioned so as to allow access to the bucky 14 to remove and insert x-ray plates indicated in phantom at 154 in FIG. 9 when the cover is in place without having to remove the cover form the bucky 14.

When the more expensive thermoplastic polycarbonate which does not lose appreciable transparency in autoclaving is utilized, the covers may be reused after autoclaving. If the less expensive polypropylene or PETG is utilized, the covers are usually disposed of after use.

While the invention has been described by reference to an illustrative embodiment, it is not intended that the novel device be limited thereby, but that modifications thereof are intended to be included as falling within the broad spirit and scope of the foregoing disclosure, the following claims and the appended drawings.

What is claimed is:

1. A sanitary shield for a dedicated mammography x-ray machine compression paddle comprising a generally rectangular pan shaped, substantially transparent non x-ray attenuating thermoplastic plastic cover having a generally flat planar surface, and walls extending normally from said planar surface to a rim, an inwardly extending flange formed integrally in said walls and spaced slightly from said rim, said walls dimensioned so as to extend around the sides of said compression paddle, said flange being dimensioned so as to slidingly engage the sides of said compression paddle and to extend over the top edge of said compression paddle sides when said cover is all the way on said compression paddle.

2. A sanitary shield for a dedicated mammography x-ray machine bucky comprising a generally rectangular pan shaped, substantially transparent non x-ray attenuating thermoplastic plastic cover having a generally flat planar surface, and walls extending normally from said planar surface to a rim, an inwardly extending flange formed integrally in said walls and spaced slightly from said rim, said walls dimensioned so as to extend around the sides of said bucky and said flange being dimensioned so as to slidingly engage the sides of said bucky and to extend over the top edge of said bucky sides when said cover all the way on said bucky.

3. A shield as claimed in claim 2 wherein the front wall of said cover extends below the lower surface of said bucky when said cover is in place on said bucky.

* * * * *